US009095489B2

(12) United States Patent
Berry et al.

(10) Patent No.: US 9,095,489 B2
(45) Date of Patent: Aug. 4, 2015

(54) SURGICAL HEAD SUPPORT ADAPTER

(75) Inventors: Joel L. Berry, Winston-Salem, NC (US); John E. Reynolds, Winston-Salem, NC (US); Charles L. Branch, Jr., Advance, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1197 days.

(21) Appl. No.: 12/670,237

(22) PCT Filed: Jul. 24, 2008

(86) PCT No.: PCT/US2008/008960
§ 371 (c)(1),
(2), (4) Date: Aug. 19, 2010

(87) PCT Pub. No.: WO2009/014721
PCT Pub. Date: Jan. 29, 2009

(65) Prior Publication Data
US 2010/0319706 A1    Dec. 23, 2010

Related U.S. Application Data

(60) Provisional application No. 60/951,569, filed on Jul. 24, 2007.

(51) Int. Cl.
*A61G 13/12*   (2006.01)
*A61G 7/07*    (2006.01)
(Continued)

(52) U.S. Cl.
CPC .............. *A61G 13/12* (2013.01); *A61G 13/121* (2013.01); *A61G 13/1205* (2013.01);
(Continued)

(58) Field of Classification Search
CPC . A61G 13/12; A61G 13/1205; A61G 13/121; A61G 13/128; A61G 13/129; A61G 2013/0036; A61G 2013/0054; A61G 2202/325; A61G 7/065; A61G 7/07; A61B 19/203
USPC .............. 128/845, 846, 870; 5/600, 621, 622, 5/630, 636–638
See application file for complete search history.

(56) References Cited

U.S. PATENT DOCUMENTS 3,188,079 A    6/1965   Boetcker et al.
4,504,050 A    3/1985   Osborne
(Continued)

FOREIGN PATENT DOCUMENTS

WO    WO 02-26188 A1      4/2002
WO    WO 2005-032416 A2   4/2005
WO    WO 2006-110671 A2   10/2006

OTHER PUBLICATIONS

International Search Report and the Written Opinion of the ISA for PCT/US2008/008960, mailed Feb. 11, 2009.

*Primary Examiner* — Alireza Nia
*Assistant Examiner* — Keri J Nielson
(74) *Attorney, Agent, or Firm* — Myers Bigel Sibley & Sajovec, PA (57) ABSTRACT

A planar support assembly for use with a patient body support, an extension support assembly, and a plurality of interchangeable head supports is provided. The extension support assembly is releasably mounted on a portion of the patient body support such that the extension support assembly extends outwardly from the patient body support. The planar support assembly includes a generally planar support configured to releasably attach to an end of the extension support assembly opposite the patient body support. The planar support is configured to receive and support one of a plurality of interchangeable head supports, and the planar support is adjustable with respect to the patient body support in two or more dimensions.

34 Claims, 6 Drawing Sheets

(51) Int. Cl.
　　*A61B 19/00* (2006.01)
　　*A61G 13/00* (2006.01)
(52) U.S. Cl.
　　CPC ............... *A61B 19/203* (2013.01); *A61G 7/07* (2013.01); *A61G 13/128* (2013.01); *A61G 13/129* (2013.01); *A61G 2013/0054* (2013.01); *A61G 2200/325* (2013.01)

(56) References Cited

U.S. PATENT DOCUMENTS

| | | |
|---|---|---|
| 4,752,064 A | 6/1988 | Voss |
| 5,483,961 A | 1/1996 | Kelley et al. |
| 5,623,949 A | 4/1997 | Kostich |
| 5,984,930 A | 11/1999 | Maciunas et al. |
| 6,112,333 A | 9/2000 | Mazzei |
| 6,306,146 B1 | 10/2001 | Dinkler |
| 6,490,737 B1 | 12/2002 | Mazzei et al. |
| 6,813,788 B2 | 11/2004 | Dinkler et al. |
| 7,117,551 B1 | 10/2006 | Dinkler, II et al. |
| 7,426,763 B2 | 9/2008 | Mazzei et al. |
| 2005/0066444 A1 | 3/2005 | Mazzei et al. |
| 2008/0078031 A1* | 4/2008 | Weinstein et al. ............ 5/630 |

* cited by examiner

SURGICAL HEAD SUPPORT ADAPTER

RELATED APPLICATIONS

This application is a 35 U.S.C. §371 national phase application of PCT Application PCT/US2008/008960, filed Jul. 24, 2008, and published in English on Jan. 29, 2009, as International Publication No. WO 2009/014721, and which claims the benefit of U.S. Provisional Patent Application Ser. No. 60/951,569, filed Jul. 24, 2007, the disclosure of each of which is incorporated herein by reference in its entirety.

FIELD OF THE INVENTION

The present invention relates to surgical head supports.

BACKGROUND OF THE INVENTION

Various devices have been developed to support a patient's head during surgery.

A ProneView® Protective Helmet System (Dupaco, Inc., Oceanside, Calif., USA) includes a tray that is supported by an underlying operating table surface. Feet project from the tray and engage or suspend a face receptacle or cushion, which is configured to receive the patient's face or head in the prone position. The feet may be adjusted to raise or lower the support cushion. The cushion typically includes a wide mask for the eyes and another outlet for tubes exiting the mouth and a mirror that allows for visualization and assessment of the patient during the procedures. Examples of devices for supporting the patient's head in the prone position include U.S. Patent Publication No. 2005/0066444 to Mazzei, U.S. Pat. No. 6,490,737 to Mazzei et al. and U.S. Pat. No. 6,112,333 to Mazzei. These devices are typically placed directly on the operating table. For example, U.S. Patent Publication No. 2005/0066444 to Mazzei includes a tray for supporting a head support, such as a ProneView® Protective Helmet System, off the table during surgeries. However, the tray in U.S. Patent Publication No. 2005/0066444 to Mazzei has very limited motion and limited options for patient positioning.

A Disposa-View™ head positioning device (Vital Signs, Inc., Totowa, N.J., USA) is a disposable head positioning device for use in surgeries in the prone position. The Disposa-View™ head positioning device includes a foam support designed to receive the patient's face or head in the prone position so that pressure around the patient's eyes and face is reduced support is provided to the head and neck.

The ProneView® head support, the Disposa-View™ head positioning device, and other similar devices are generally used in thoracic and lumbar procedures such that the tray or base of the ProneView® head support or the Disposa-View™ head positioning device is supported by the operating table surface. However, in many procedures (such as procedures relating to the cervical spine), it is desirable for the patient's head to rest off the end of the table. For example, the patient's head may be placed on a support that extends away from the operating table. One example of such an off-the-table support is the Mayfield® headholder (Integra Lifesciences Corporation, Cincinnati, Ohio, USA). The Mayfield® headholder is a type of head support device that is typically mounted on a crossbar or other support that extends transversely off the end of an operating table. See U.S. Pat. No. 5,984,930 to Maciunas, U.S. Pat. No. 6,813,788 to Dinkier et al., U.S. Pat. No. 3,188,079 to Boetcker et al. and U.S. Pat. No. 7,117,551 to Dinkier et al.

The Mayfield® headholder can provide a wide range of motion and/or relatively secure head stabilization. For example, a clamp with three sterile pins can be driven into the skull to secure the patient's head. In particular, the pins are inserted through the scalp into the outer portion of the skull. In some cases, clamping the pins into the cranium can cause tissue injury, lacerations, and the like. Alternatively, a horseshoe holder, which fits tightly over the forehead and around the eyes, is used. However, this configuration may be a compression threat to the patient's eyes and soft tissue of the face. For example, excessive compression of the eyes can cause blindness or vision damage, and excessive compression of the soft tissue of the face can cause bruising and sores.

SUMMARY OF THE INVENTION

According to some embodiments of the current invention, a patient support system includes a patient body support and a patient head support system releasably mounted on a portion of the patient body support. The patient head support system includes an extension support assembly having first and second ends. The first end is releasably mounted on a portion of the patient body support such that the extension support assembly extends outwardly from the patient body support. The patient head support system includes a generally planar support at the second end of the extension support assembly. The planar support is configured to receive and support one of a plurality of interchangeable head supports. The planar support is adjustable with respect to the patient body support in two or more dimensions.

According to further embodiments according to the invention, a head support system for use with a patient body support and a plurality of interchangeable head supports includes an extension support assembly having first and second ends. The first end of the extension support assembly is configured to be mountable on a portion of the patient body support such that the extension support assembly extends outwardly from the patient body support. A generally planar support is at the second end of the extension support assembly. The planar support is configured to receive and support one of a plurality of interchangeable head supports.

In certain embodiments, the patient body support is an operating table and the plurality of interchangeable head supports are configured to alternatively rest on either the planar support or the operating table.

In particular embodiments, the plurality of interchangeable head supports can include a generally planar base, and the planar support can include a notch configured to receive a portion of the planar base therein. The planar support can include one or more securing members configured to secure the generally planar base of the head support on the planar support. The securing members can be screws.

In some embodiments according to the invention, the position of the planar support can be moveable in three dimensions and/or can be rotatable with respect to the patient body support.

In particular embodiments, the extension support assembly includes a pair of support shafts mounted to the patient body support and extending substantially parallel to a length of the patient body support and a guide rod transversely mounted on the pair of support shafts. The generally planar support is slideably mounted on the guide rod. The generally planar support can be pivotably mounted on the guide rod. The generally planar support can be mounted to the guide rod by a support mounting rod that is configured to move the generally planar support in a generally vertical an/or rotational direction.

In still further embodiments of the current invention, a planar support assembly for use with a patient body support, an extension support assembly, and a plurality of interchangeable head supports is provided. The extension support assembly is releasably mounted on a portion of the patient body support such that the extension support assembly extends outwardly from the patient body support. The planar support assembly includes a generally planar support configured to releasably attach to an end of the extension support assembly opposite the patient body support. The planar support configured to receive and support one of a plurality of interchangeable head supports. The planar support is adjustable with respect to the patient body support in two or more dimensions.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS

According to the Invention

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

This application is related to U.S. Design Application Ser. No. 29/299,307, filed Dec. 21, 2007, the disclosure of which is hereby incorporated by reference in its entirety.

With reference to FIGS. 1-4, a head support system 10 according to embodiments of the current invention is mounted on a patient body support or operating table 400.

The head support system 10 includes an extension support assembly 200 having two ends 212, 214. The end 212 of the extension support assembly 200 is configured to be mountable on a portion of the operating table 400 such that the extension support assembly 200 extends outwardly from the operating table 400. The other end 214 of the extension support assembly 200 has a planar support member 350 for holding a head support 100 thereon. As illustrated, the planar member 350 is provided as part of a planar support mounting assembly 300 that is configured to releasably attach to the end 214 of the extension support assembly 200.

The extension support assembly 200 includes support shafts 216, 218, a guide rod 220, three support arm members 222, 224, 226, a closing handle 228 and a receptacle 230. The support shafts 216, 218 extend away from the operating table 400 in a horizontal direction, and the guide rod 220 extends in a transverse direction with respect to the table 400 (i.e., parallel to a width dimension of the table 400). The arm member 222 provides a slidable connection to the guide rod 220 so that the planar member 350 may be moved in a direction parallel to the guide rod 220. The arm member 222 is also rotatable with respect to the arm member 224 by releasing the closing handle 228, which simultaneously locks the orientation of the arm member 222 with respect to the guide rod 220 and the arm member 224. Accordingly, the extension support assembly 200 is configured to move the planar member 350 with respect to the operating table 400 and to secure the planar member 350 in a desired orientation. The extension support assembly 200 may incorporate certain features of a Mayfield® headholder (Integra Lifesciences Corporation, Cincinnati, Ohio, USA) and/or the systems disclosed in U.S. Pat. No. 7,117,551 to Dinkler, II et al. and U.S. Pat. No. 5,564,663 to Cook et al., the disclosures of which are incorporated by reference herein in their entireties. The receptacle 230 is configured to mate with a corresponding mounting receptacle 362 on the planar support mounting assembly 300. In some embodiments, the extension support assembly 200 and/or the planar support assembly 300 can incrementally reposition a patient during surgery.

The head support 100 includes a face receptacle 102 with facial pads 104 positioned on the interior surface of the face receptacle 102 to receive and hold the face of the patient in the prone position. As illustrated, the head support 100 further includes face receptacle supports 106, a base member 108 and a mirror 110. The head support 100 is configured to alternatively rest on either the planar member 350 or the table 400. Thus, a head support 100 that may be generally designed for use on the table 400 can also be used in an off-table position, i.e., on the planar member 350, to permit increased versatility in positioning the patient for surgery. The face receptacle supports 106 are between the base member 108/mirror 110 and the head support. The face receptacle 102 includes sufficient apertures 102A to generally correspond to the patient's eyes and/or mouth and/or provide an access area for any desired medical equipment, such as surgical tubes, exiting the mouth. The mirror 110 allows medical health professionals to view and monitor the patient during the procedure. In this configuration, a plurality of different head supports (such as the head support 100) can be placed on the planar member 350. In particular embodiments, the head supports are configured to rest alternately on either the planar member 350 or the operating table 400. For example, the head support 100 may be a ProneView® head support by Dupaco, Inc. (Oceanside, Calif., USA), which is generally designed to be used on an operating table. See U.S. Pat. No. 6,490,737 and U.S. Patent Application Publication No. 2005/0066444 to Mazzei et al., the disclosures of which are hereby incorporated by reference in their entireties. Other head supports can be used, including any suitable head support that is configured to rest on a generally planar surface, such as the Disposa-View™ (Vital Signs, Inc., Totowa, N.J., USA). Accordingly, the head of the patient can rest off of the operating table 400, for example, during various surgical procedures. Examples of surgical procedures in which the head of the patient may rest off of the operating table 400 include cervical spine decompression and/or fusion surgeries (such as posterior cervical decompression and fusion), cervical spine fracture fixation and fusion surgeries (such as cervical open reduction internal fixation (ORIF)), posterior cervical discectomy, foramen magnum decompression for Chiari or occipital cervical procedures and/or foramen magnum cerebellar tonsillar herniation surgeries.

Figure 1:
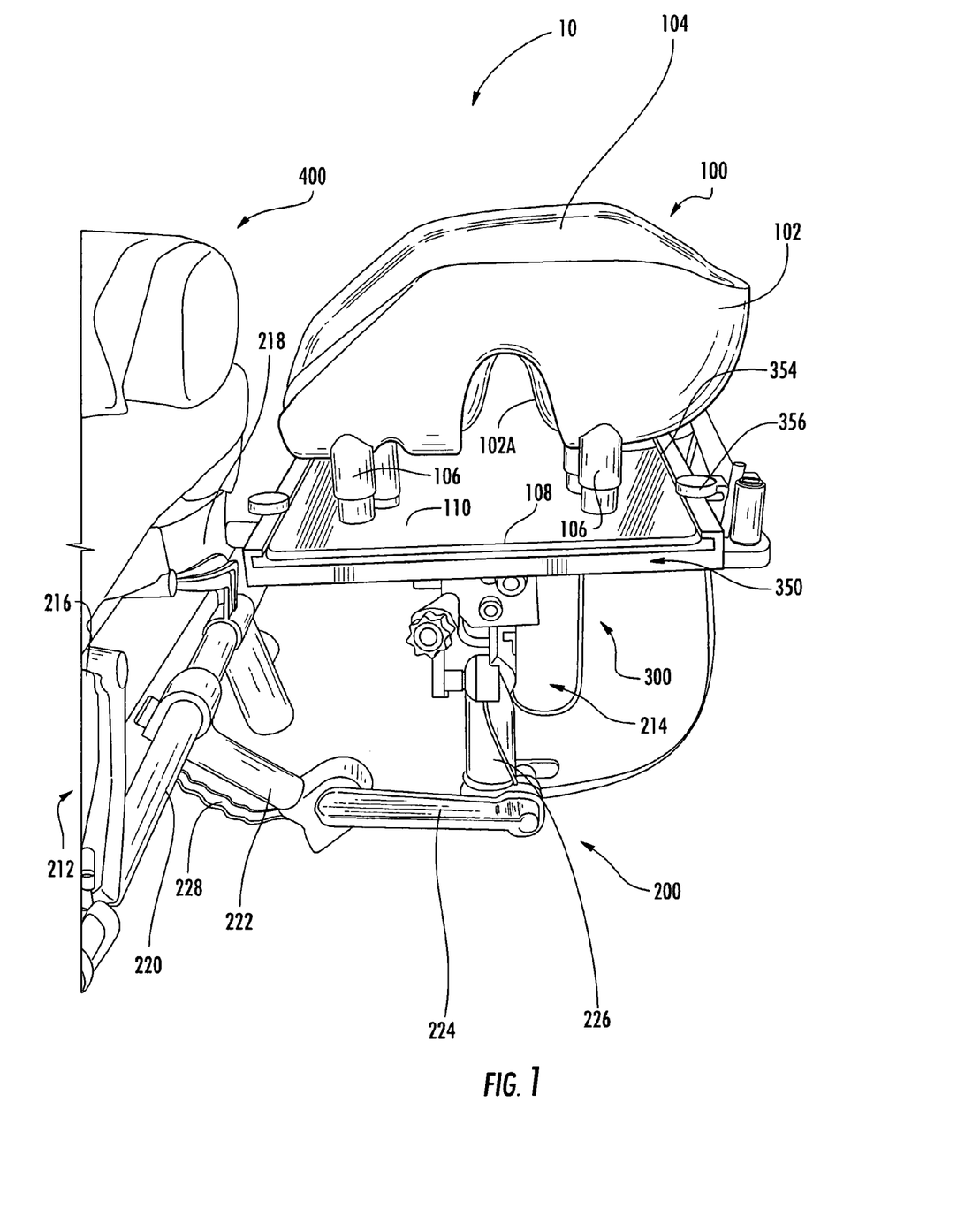
FIG. 1 is a side view of a head support system having a planar support assembly according to embodiments of the current invention.
Figure 2:
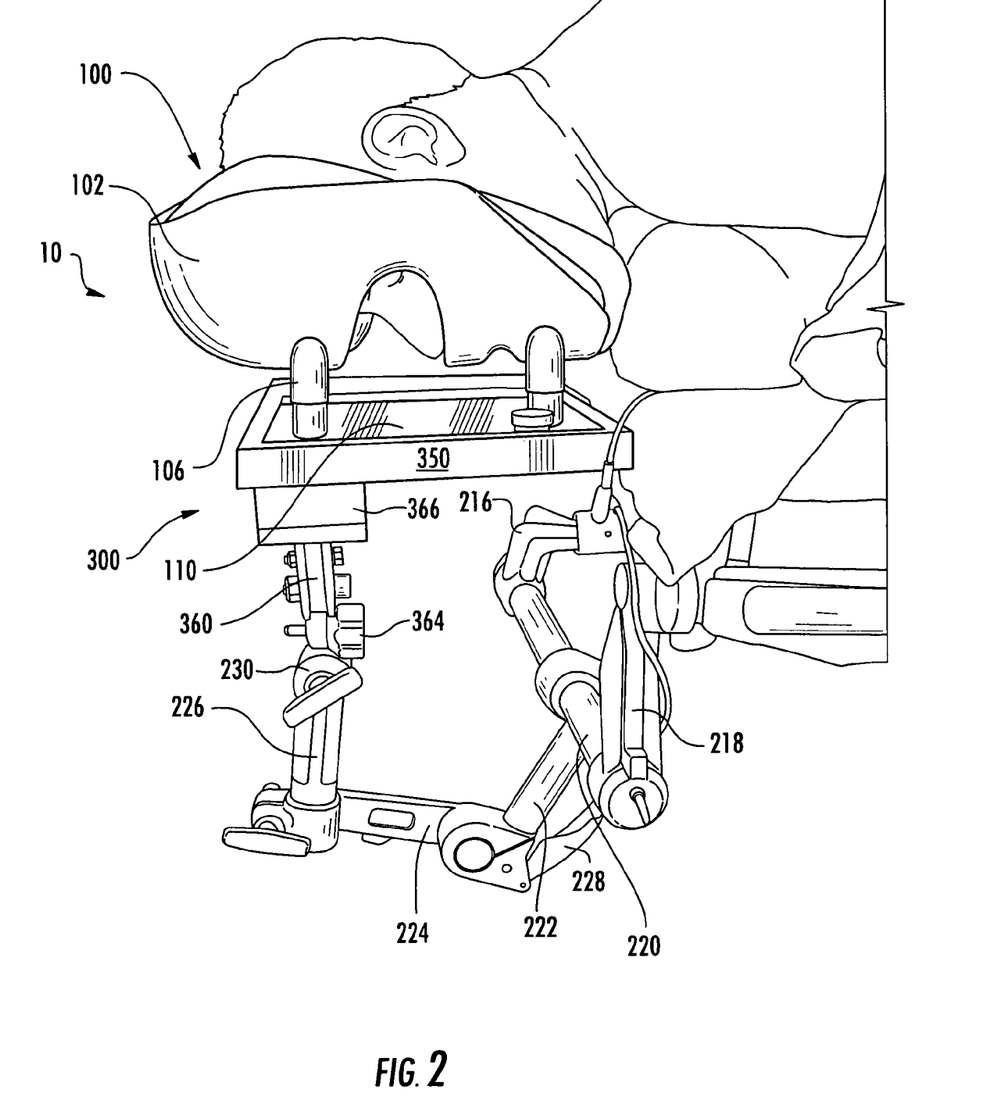
FIG. 2 is an opposing side view of the head support system of FIG. 1.
Figure 3:
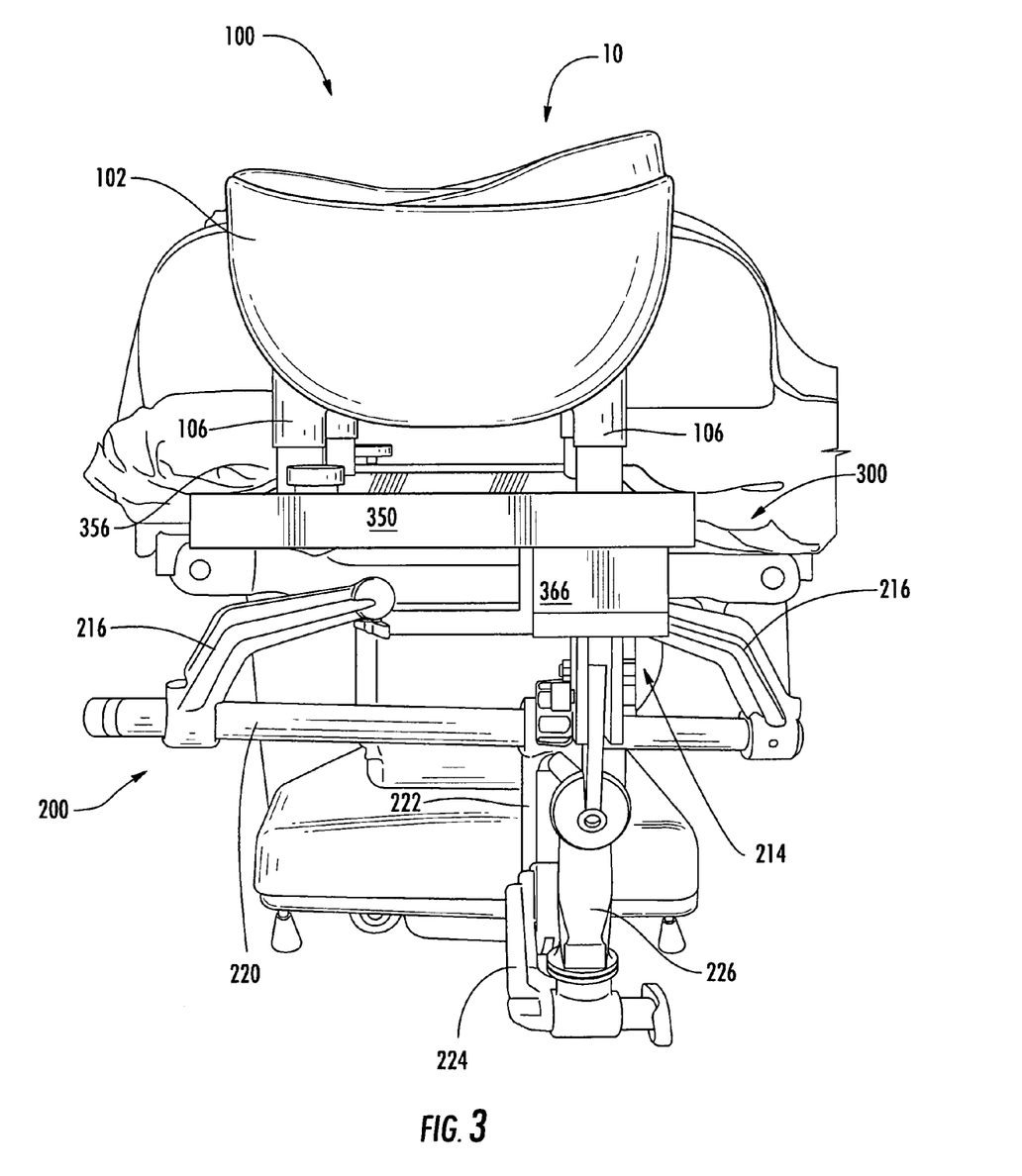
FIG. 3 is a front side view of the head support system of FIG. 1.

As illustrated in FIGS. 1-3, the patient can be positioned with the head off of the operating table 400 without requiring that sterile pins be driven into the skull of the patient to secure the patient's head. In addition, use of a conventional "horseshoe" head holder, which fits tightly over the forehead and eyes (causing a potential threat of compression to the patient's facial/eye area), may be obviated. In contrast to skull pin and horseshoe configurations typically used with a Mayfield® head holder, the interchangeable head supports described herein (such as the head support 100) can include a generally flat base member 108 that supports a face receptacle 102. The face receptacle 102 includes openings 102A and is separated from the base member 108 by the supports 106 such that medical health professionals may view and monitor the patient in the mirror 110, and an access area is provided around the patient's eyes and/or mouth to permit space for any desired medical equipment, such as surgical tubes exiting the mouth. For example, head supports that are configured to rest on the operating table can be used in a configuration as illustrated in FIGS. 1-3 where the patient's head rests off of the operating table on the planar member 350.

In some embodiments, the patient is in the prone position, and medical health professionals can move the patient's head vertically, horizontally, or rotationally in substantially all directions. Real time images, such as real time X-ray fluoroscopic images can also be used to guide and/or optimize head, neck and/or spine placement for surgery. For example, the planar support 350 and/or other components of the planar support mounting assembly 300 (or head support 100) can be formed of a radiolucent material, such as carbon fiber, organic polymers, composites thereof, etc. The support can be formed in whole or in part of such radiolucent material, so long as a sufficient portion is formed of such material to permit imaging access of the cervical spine of the patient when the device is positioned and used as described herein. In some embodiments, the planar support mounting assembly 300 can be positioned with respect to the head support 100 to facilitate imaging the patient. For example, as illustrated in FIG. 3, the spacer 366 is offset to the side of the planar support 350, which can provide imaging access for anterior and posterior imaging of the spine. In some embodiments, the spacer 366 can be movably attached to the planar support 350, for example, by a slide such as a dovetail slide, such that the distance that the spacer 366 is offset can be adjusted.

Figure 4:
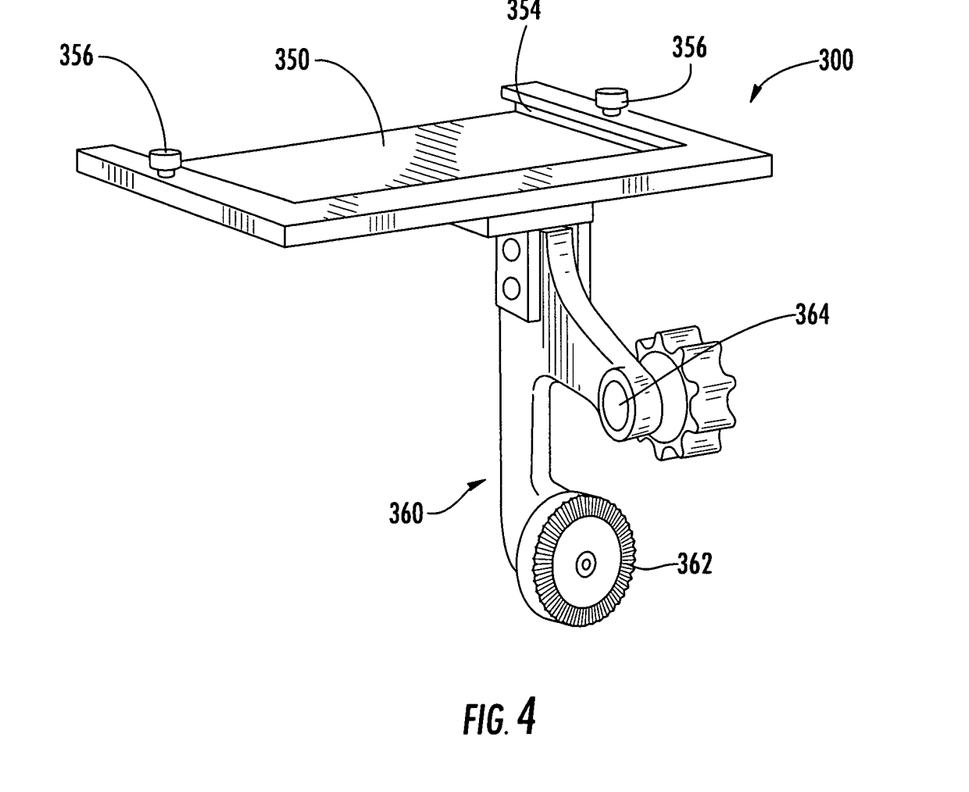
FIG. 4 is a side perspective view of the planar support assembly of the head support system of FIG. 1.

With reference to FIG. 4, the planar support mounting assembly 300 includes the planar support 350, a mounting arm 360, a mounting receptacle 362 and a receptacle 364. The planar member 350 includes a notch 354 and securing members or pins 356. In this configuration, and as shown in FIGS. 1-3, the base member 108 of the head support 100 can be received in the notch 354, which extends around at least a portion of the perimeter of the planar member 350. The pins 356 may be tightened to secure the base member 108 of the head support 100 adjacent the planar member 350. The receptacle 364 can receive other surgical equipment therein, including traction arms or the like. As shown in FIGS. 2-3, the planar support mounting assembly 300 can include an optional spacer 366 between the mounting arm 360 and the planar support 350 that increases the height of the planar support 350.

Although the planar support 350 is illustrated in FIGS. 1-4 with respect to the planar support mounting assembly 300, the extension support assembly 200, and/or the head support 100, it should be understood that other configurations can be used. For example, various configurations can be used to releasably attach the planar support 350 to the operating table 400 or other patient body support. Alternatively, the planar support 350 may be permanently mounted on the operating table 400 or on the extension support assembly 200. In some embodiments, the planar support assembly 300 (including the planar support 350) and the extension support assembly 200 can be combined to form a single unit that is releasably mounted on the table 400. The planar support 350 can be used to support one of a plurality of interchangeable head supports (such as head support 100) so that the patient's head rests off of the operating table 400. This configuration may be particularly useful in procedures relating to the cervical spine, in which the patent's head generally is supported adjacent to the operating table.

The planar support 350 can be used to support various types of head rests (such as head support 100), including head supports that are generally designed to rest on the operating table 400. Accordingly, head supports that have been designed for "on-table" use may be used in generally the configuration shown in FIG. 1-3 such that the patient's head is supported off the operating table 400. Any suitable patient body support or operating table can be used, including different operating beds, Jackson tables, etc.

In some embodiments, the position of the planar support 350 is adjustable with respect to the operating table 400. For example, as illustrated in FIGS. 1-3, the planar support 350 can be movable in one, two or three dimensions and is rotatable with respect to the operating table 400. Head supports (such as head support 100) that are generally designed to rest on an operating table may be movably attached adjacent the operating table, which can allow increased flexibility in positioning a patient's head during surgeries.

Although the patient support assembly 300 is illustrated with a notch 354 and fastening screws or pins 356, other configurations can be used to secure the head support 100 to the planar member 350. For example, an adhesive may be used on the surface of the planar member 350 and/or base mirror 110 of the head support 100 or the planar member 350 can include a textured surface to reduce slippage of the head support 100. In some embodiments, head support 100 merely rests on the planar member 350 without being actively secured thereto.

Various configurations of planar supports can be used without departing from the scope of the current invention, including planar supports that can be releasably attached to an extension support assembly, such as the extension support assembly 200. Various adjustment arms, knobs, and other adjustable supports can also be used.

For example, a planar member mounting assembly 500 including a planar member 550 is shown in FIGS. 5-8. The planar member 550 is attached to a standoff spacer 554 and a receptacle 556. The planar member mounting assembly 500 includes an articulating spacer arm 570 that has a plurality of receptacles 572A-572C that are configured to connect to mating receptacles. For example, as illustrated, the receptacle 572A releasably connects with the receptacle 556 (see FIG. 8), the receptacle 572B releasable connects to a traction device or traction arm (not shown), and the receptacle 572C releasable connects to the extension support assembly 200 at the receptacle 230 (FIGS. 1-4). In some embodiments, the receptacles 556 and 572A-572C permit attachment at a various angles. For example, the receptacles 556 and 572A can be positioned to attach the planar member 550 at a desired rotational orientation with respect to the articulating spacer arm 570.

As shown in FIGS. 5-8, the articulating spacer arm 570 includes a shaft 574 with an adjustable pin 576 that is operatively connected to an adjustment knob 578 and set screw 578A. When the adjustment knob 578 is in a loose position and the set screw 578A does not contact the pin 576, the shaft 574 rotates and/or moves horizontally to adjust a height and/or rotational orientation of the planar member 550, e.g., to facilitate placement of the patient on the table 400 of FIGS. 1-3. The shaft 574 may be secured in a desired position by tightening the adjustment knob 578 so that the set screw 578A contacts and secures the pin 576 with respect to the shaft 574.

Figure 5:
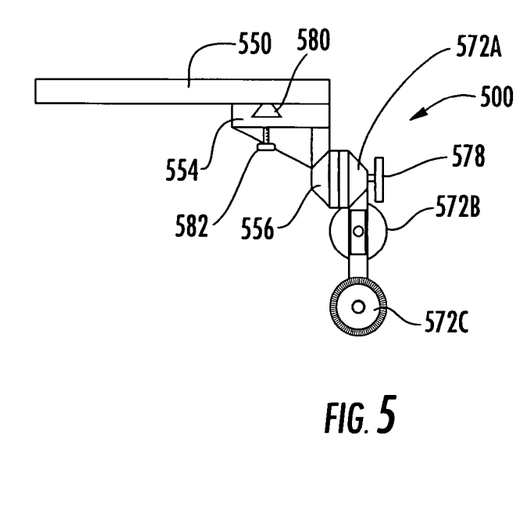
FIG. 5 is a side view of a planar support assembly according to embodiments of the present invention.
Figure 6:
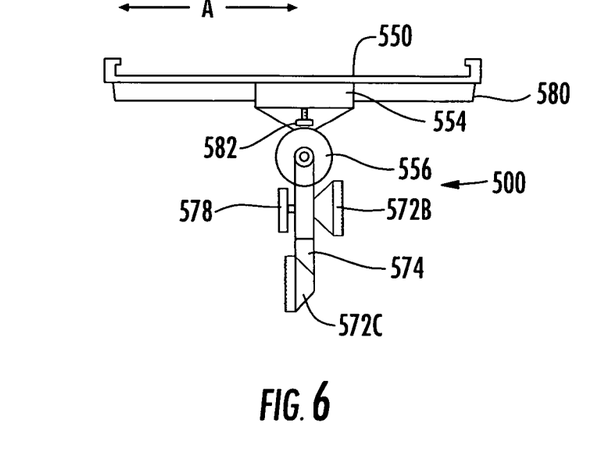
FIG. 6 is a front side view of the planar support assembly of FIG. 5.
Figure 7:
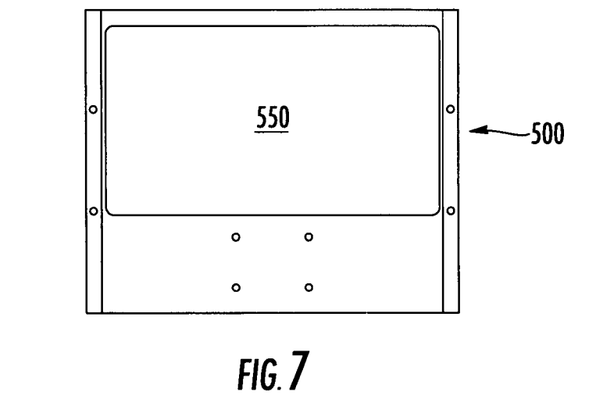
FIG. 7 is a top view of the planar support assembly of FIG. 5.
Figure 8:
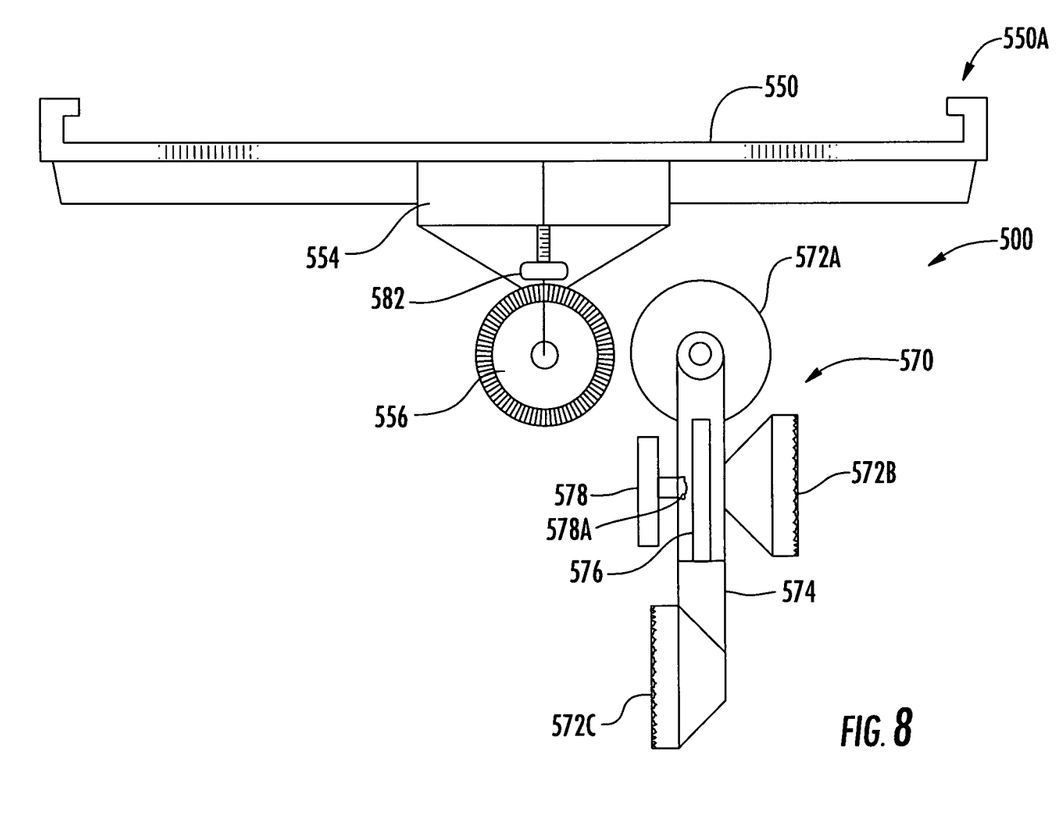
FIG. 8 is an exploded top view of the planar support assembly of FIG. 5.

In some embodiments, the planar mounting assembly 500 includes a side-to-side mechanism, such as a dovetail slide 580, which is configured to move the planar member 550 of the assembly 500 in a direction along arrow A with respect to the spacer 554 and articulating spacer arm 570. As illustrated in FIG. 5, the slide 580 includes a knob 580 that is attached to a screw (not shown), which can be tighten to hold the slide 580 in a desired fixed position with respect to the spacer 554.

Orientation and placement may be facilitated by the use of a real-time imaging apparatus as noted above to optimize the position of cervical vertebrae for surgery thereon, such as for cervical spine decompression and/or fusion; cervical spine fracture fixation and fusion and corrective surgery for cerebellar tonsillar herniation. Optimal positioning of the patient's head and neck can be achieved for cervical spine correction and/or to optimize positioning for cranio-cervical decompression of fusion.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A planar support assembly for use with a patient body support, an extension support assembly, and a plurality of interchangeable head supports, wherein the extension support assembly is releasably mounted on a portion of the patient body support such that the extension support assembly extends outwardly from the patient body support, the planar support assembly comprising:

a generally planar support configured to releasably attach to an end of the extension support assembly opposite the patient body support, the planar support configured to receive and support one of the plurality of interchangeable head supports, wherein the planar support is adjustable with respect to the patient body support in two or more dimensions, wherein the patient body support is an operating table and the plurality of interchangeable head supports are configured to alternatively rest on either the planar support or the operating table and one of the plurality of interchangeable head supports includes a generally planar base and the planar support further comprises a notch configured to receive a portion of the planar base therein.

2. The planar support assembly of claim 1, wherein the plurality of interchangeable head supports each include a face receptacle configured to receive and hold a face of a patient in the prone position, wherein the face receptacle includes a first aperture sized and configured to generally correspond to a patient's eyes and a second aperture sized and configured to generally correspond to a patient's mouth and to provide an access area for surgical tubes exiting the patient's mouth.

3. The planar support assembly of claim 2, wherein the plurality of interchangeable head supports each include a base member configured to alternatively rest on either the planar support or the operating table and a plurality of face receptacle supports between the base member and the face receptacle.

4. The planar support assembly of claim 1, wherein the planar support further comprises one or more securing members configured to secure the generally planar base of one of the plurality of head supports on the planar support.

5. The planar support assembly of claim 1, further comprising an articulating spacer arm connected to the generally planar support and configured to move the generally planar support in a generally vertical and/or rotational direction with respect to the patient body support.

6. The planar support assembly of claim 5, wherein the articulating spacer arm is connected to the generally planar support in an offset position configured to provide imaging access for anterior and posterior imaging of a cervical spine of a patient.

7. The planar support assembly of claim 5, further comprising a slide member configured to move the generally planar support in a horizontal direction with respect to the articulating spacer arm.

8. The planar support assembly of claim 1, wherein the planar support is radiolucent.

9. The patient support system of claim 1, wherein the planar support further comprises one or more securing members configured to secure the generally planar base of one of the plurality of head supports on the planar support.

10. The patient support system of claim 9, wherein the securing members are screws.

11. A head support system for use with a patient body support and a plurality of interchangeable head supports, the head support system comprising:
  an extension support assembly having first and second ends, wherein the first end is configured to be mountable on a portion of the patient body support such that the extension support assembly extends outwardly from the patient body support; and
  a generally planar support mounted at the second end of the extension support assembly, the planar support configured to receive and support one of the plurality of interchangeable head supports;
  wherein the planar support is adjustable with respect to the patient body support in two or more dimensions and one of the plurality of head supports includes a generally planar base and the planar support further comprises a notch configured to receive a portion of the planar base therein.

12. The head support system of claim 11, wherein the patient body support is an operating table and the plurality of interchangeable head supports are configured to alternatively rest on either the planar support or the operating table.

13. The head support system of claim 12, wherein the plurality of interchangeable head supports each include a face receptacle configured to receive and hold a face of a patient in the prone position, wherein the face receptacle includes a first aperture sized and configured to generally correspond to a patient's eyes and a second aperture sized and configured to generally correspond to a patient's mouth and to provide an access area for surgical tubes exiting the patient's mouth.

14. The head support system of claim 13, wherein the plurality of interchangeable head supports each include a base member configured to alternatively rest on either the planar support or the operating table and a plurality of face receptacle supports between the base member and the face receptacle.

15. The head support system of claim 11, wherein the planar support further comprises one or more securing members configured to secure the generally planar base of one of the plurality of head supports on the planar support.

16. The head support system of claim 15, wherein the securing members are screws.

17. The head support system of claim 11, wherein the position of the planar support is moveable in three dimensions with respect to the patient body support.

18. The head support system of claim 11, wherein the position of the planar support is rotatable with respect to the patient body support.

19. The head support system of claim 11, wherein the extension support assembly includes:
  a pair of support shafts mounted to the patient body support and extending substantially parallel to a length of the patient body support; and
  a guide rod transversely mounted on the pair of support shafts, wherein the generally planar support is slideably mounted on the guide rod.

20. The head support system of claim 19, wherein the generally planar support is pivotably mounted on the guide rod.

21. The head support system of claim 19, wherein the generally planar support is mounted to the guide rod by a support mounting rod that is configured to move the generally planar support in a generally vertical and/or rotational direction.

22. The head support system of claim 11, further comprising an articulating spacer arm between the extension support assembly and the generally planar support configured move the generally planar support in a generally vertical and/or rotational direction.

23. The head support system of claim 22, further comprising a slide member configured to move the generally planar support in a horizontal direction with respect to the articulating spacer arm.

24. A patient support system comprising:
  a patient body support; and
  a patient head support system releasably mounted on a portion of the patient body support, the patient head support system comprising:
    an extension support assembly having first and second ends, wherein the first end is releasably mounted on a portion of the patient body support such that the extension support assembly extends outwardly from the patient body support; and a generally planar support mounted at the second end of the extension support assembly, the planar support configured to receive and support one of a plurality of interchangeable head supports, wherein the planar support is adjustable with respect to the patient body support in two or more dimensions and one of the plurality of head supports includes a generally planar base and the planar support further comprises a notch configured to receive a portion of the planar base therein.

25. The patient support system of claim 24, wherein the patient body support is an operating table and the plurality of interchangeable head supports are configured to alternatively rest on either the planar support or the operating table.

26. The patient support system of claim 25, wherein the plurality of interchangeable head supports each include a face receptacle configured to receive and hold a face of a patient in the prone position, wherein the face receptacle includes a first aperture sized and configured to generally correspond to a patient's eyes and a second aperture sized and configured to generally correspond to a patient's mouth and to provide an access area for surgical tubes exiting the patient's mouth.

27. The patient support system of claim 26, wherein the plurality of interchangeable head supports each include a base member configured to alternatively rest on either the planar support or the operating table and a plurality of face receptacle supports between the base member and the face receptacle.

28. The patient support system of claim 24, wherein the position of the planar support is moveable in three dimensions with respect to the patient body support.

29. The patient support system of claim 24, wherein the position of the planar support is rotatable with respect to the patient body support.

30. The patient support system of claim 24, wherein the extension support assembly includes:

a pair of support shafts mounted to the patient body support and extending substantially parallel to a length of the patient body support; and a guide rod transversely mounted on the pair of support shafts, wherein the generally planar support is slideably mounted on the guide rod.

31. The patient support system of claim 30, wherein the generally planar support is pivotably mounted on the guide rod.

32. The patient support system of claim 30, wherein the generally planar support is mounted to the guide rod by a support mounting rod that is configured to move the generally planar support in a generally vertical an/or rotational direction.

33. The patient support system of claim 24, further comprising an articulating spacer arm between the extension support assembly and the generally planar support configured move the generally planar support in a generally vertical and/or rotational direction.

34. The patient support system of claim 33, further comprising a slide member configured to move the generally planar support in a horizontal direction with respect to the articulating spacer arm.

* * * * *

UNITED STATES PATENT AND TRADEMARK OFFICE
CERTIFICATE OF CORRECTION

PATENT NO. : 9,095,489 B2  
APPLICATION NO. : 12/670237  
DATED : August 4, 2015  
INVENTOR(S) : Berry et al.

Page 1 of 1

It is certified that error appears in the above-identified patent and that said Letters Patent is hereby corrected as shown below:

<u>On Title Page:</u>
Item 75, Inventors:
  Please correct "Joel L. Berry, Winston-Salem, NC (US)"
    to read -- Joel L. Berry, Birmingham, AL (US) --

<u>In the Specification:</u>
Column 2, Line 64: Please correct "vertical an/or rotational"
    to read -- vertical and/or rotational --

<u>In the Claims:</u>
Column 12, Line 20: Please correct "vertical an/or rotational"
    to read -- vertical and/or rotational --

Signed and Sealed this
Twenty-sixth Day of April, 2016

Michelle K. Lee
*Director of the United States Patent and Trademark Office*